United States Patent [19]

Pelosi, Jr.

[11] 4,002,620
[45] Jan. 11, 1977

[54] 2-ANILINO-4H-3,1-BENZOTHIAZINES

[75] Inventor: Stanford S. Pelosi, Jr., Norwich, N.Y.

[73] Assignee: Morton-Norwich Products, Inc., Norwich, N.Y.

[22] Filed: Oct. 30, 1975

[21] Appl. No.: 627,228

[52] U.S. Cl. .......................... 260/243 R; 424/246
[51] Int. Cl.[2] ...................................... C07D 279/08
[58] Field of Search ................................ 260/243 R

[56] References Cited
UNITED STATES PATENTS 3,417,085  12/1968  Kuch et al. .................. 260/243

Primary Examiner—John M. Ford
Attorney, Agent, or Firm—Anthony J. Franze

[57] ABSTRACT

Certain 2-anilino-4H-3,1-benzothiazines of the formula:

wherein $R_1$ is hydrogen and $R_2$ is 4-dimethylamino, 5-chloro-2,4-dimethoxy or 3,4-dichloro; and $R_1$ is chloro and $R_2$ is 4-acetyl or 3-chloro are effective anthelmintic agents.

7 Claims, No Drawings

2-ANILINO-4H-3,1-BENZOTHIAZINES

This invention relates to chemical compounds. More particularly this invention relates to certain 2-anilino-4H-3,1-benzothiazines of the formula:

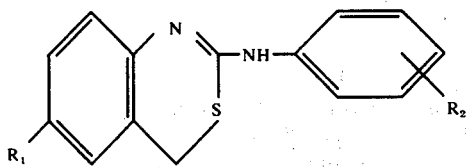

wherein $R_1$ is hydrogen and $R_2$ is 4-dimethylamino, 5-chloro-2,4-dimethoxy or 3,4-dichloro; and $R_1$ is chloro and $R_2$ is 4-acetyl or 3-chloro and a method for their preparation.

These compounds are distinguished by their ability to combat helminth infection. When administered by gavage as a suspension in aqueous solution to mice harboring Ascaris suum worms, these compounds, is a dose of 100 mg/kg, accomplish a 33–69% reduction of the worm burden.

The compounds of this invention are readily prepared. Currently it is preferred to prepare these compounds according to the following schema:

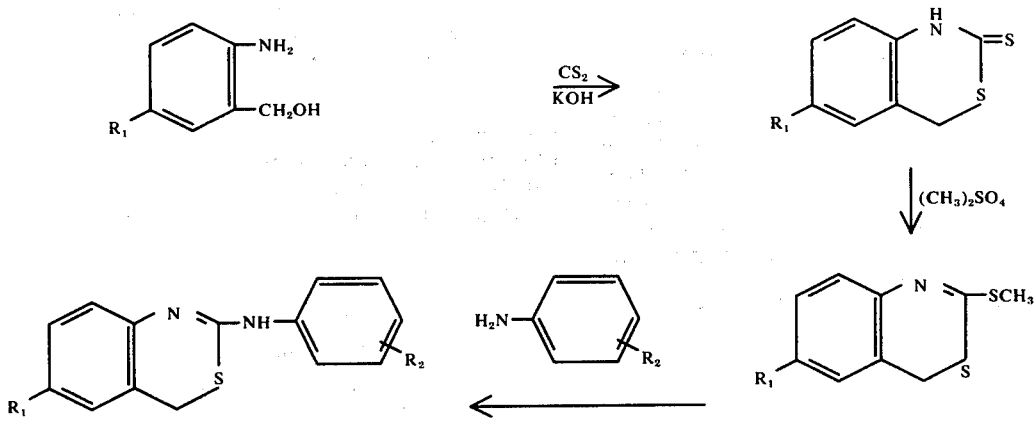

In the above schema, $R_1$ and $R_2$ have the significance previously ascribed. In order that this invention may be fully available to and understood by those skilled in the art, the following examples ae supplied.

EXAMPLE I 2-(4-Dimethylaminoanilino)-4H-3,1-benzothiazine Dihydrochloride

A mixture of 9.7 g (0.05 mole) of 2-methylthio-4H-3,1-benzothiazine and 6.8 g (0.05 mole) of N,N-dimethyl-p-phenylenediamine in 50 ml of n-butanol was heated under reflux for 17 hours. After cooling in ice, the solid was collected by filtration and recrystallized from ethanol to give 8.3 (58%) of the free base. A suspension of the free base in 50 ml of acetonitrile was treated with hydrogen chloride and heated to boiling. Absolute ethanol was added for dissolution. With cooling in ice and the addition of anhydrous ether, a solid separated which was collected by filtration to give 9.4 g (53%) of product, m.p. 180°–238° (dec.).

Anal. Calcd. for $C_{16}H_{17}N_3S \cdot 2HCl$: C, 53,93; H, 5.37; N, 11.79; S, 9.00; Cl, 19.90.

Found: C, 53.80; H, 5.42; N, 11.87; S, 9.11, 9.09; Cl, 19.79, 19.84.

EXAMPLE II 2-(5-Chloro-2,4-dimethoxyanilino)-4H-3,1-benzothiazine

A mixture of 2-methylthio-4H-3,1-benzothiazine (48.8 g, 0.25 mole) and 5-chloro-2,4-dimethoxyaniline (46.8 g, 0.25 mole) in n-butanol (200 ml) was refluxed overnight. After cooling in ice, the solid was collected by filtration and recrystallized from ethanol to give 36 g (43.4%) of product. Recrystallization from ethanol gave an analytical sample, m.p. 157°–158°.

Anal. Calcd. for $C_{16}H_{15}ClN_2O_2S$: C, 57.39; H, 4.51; N, 8.36.

Found: C, 57.24; H, 4.52; N, 8.34.

EXAMPLE III 2-(3,4-Dichloroanilino)-4H-3,1-benzothiazine

A mixture of 2-methylthio-4H-3,1-benzothiazine (39 g, 0.20 mole) and 3,4-dichloroaniline (32.4 g, 0.20 mole) in n-butanol (150 ml) was refluxed overnight. After cooling in ice, the solid was collected by filtration and recrystallized from ethanol to give 27 g (43.8%) of product. Recrystallization from ethanol gave analytical sample m.p. 207°–208°.

Anal. Calcd. for $C_{14}H_{10}Cl_2N_2S$: C, 54.38; H, 3.26; N, 9.06.

Found: C, 54.33; H, 3.24; N, 9.12.

EXAMPLE IV

6-Chloro-4H-3,1-benzothiazine-2(1H)thione

Carbon disulfide (180 ml, 3.0 moles) was added dropwise to a stirred solution of 84 g (1.5 moles) of potassium hydroxide in 400 ml of absolute ethanol with external cooling. To this mixture was added 157 g (1.0 mole) of 2-amino-5-chlorobenzyl alcohol. The reaction mixture was heated under reflux for 20 hours and the solvent was removed by distillation. The solid residue was stirred with 2000 ml of 10% aqueous potassium hydroxide, and the mixture was filtered to remove neutral impurities. The clear filtrate was made acidic with dil. hydrochloric acid, and the solid which was deposited was collected by filtration to give 221 g (100%) of product. Recrystallization from methanol gave an analytical sample, m.p. 217°–222°.

Anal. Calcd. for C$_8$H$_6$NS$_2$Cl: C, 44.54; H 2.80; N, 6.49;
S, 29.73; Cl, 16.44.
Found: C, 44.79; H, 2.87; N, 6.46;
S, 29.84, 29.67; Cl, 16.63, 16.45.

6-Chloro-2-methythio-4H-3,1-benzothiazine Hydrochloride

Dimethyl sulfate (34 ml, 0.36 mole) was added dropwise to a stirred mixture of 77 g (0.36 mole) of the above compound in 150 ml (0.36 mole) of 10% sodium hydroxide solution with external cooling to maintain the temperature below 40°. The mixture was stirred at ambient temperature for 4 hours, and the solid was collected by filtration to give 80 g (96%) of yellow solid. Recrystallization from a methanol-water mixture gave 43 g (52%) of the free base of product. A suspension of 3.0 g (0.013 mole) of the free base in 25 ml of acetonitrile was treated with hydrogen chloride and heated to boiling. Additional acetonitrile and absolute ethanol were added for dissolution. With cooling in ice and the addition of anhydrous ether, a solid separated which was collected by filtration to give 2.3 g (66%) of product, m.p. 134°–137°.

Anal. Calcd. for C$_9$H$_8$ClNS$_2$·HCl: C, 40.60; H, 3.41; N, 5.26
S, 24.09; Cl, 26.64.
Found: C, 40.78; H, 3.48; N, 5.33
S, 24.06, 24.10; Cl, 26.63, 26.69.

2-(4-Acetylanilino)-6-chloro-4H-3,1-benzothiazine

A mixture of 6-chloro-2-methylthio-4H-3,1-benzothiazine (57.5 g, 0.25 mole) and p-aminoacetophenone (33.8 g, 0.25 mole) in n-butanol (200 ml) was refluxed overnight. After cooling in a refrigerator for three days, the solid was collected by filtration and recrystallized from ethanol-water mixture to yield 31 g (39%) of product. Recrystallization from ethanol-water mixture gave an analytical sample, m.p. 174°–175°.

Anal. calcd. for C$_{16}$H$_{13}$ClN$_2$OS: C, 60.65; H, 4.13; N, 8.84.
Found: C, 60.39; H, 4.21; N, 8.49.

EXAMPLE V

6-Chloro-2-(3-chloroanilino)-4H-3,1-benzothiazine

A mixture of 6chloro-2-methylthio-4H-3,1-benzothiazine (69 g, 0.30 mole) and 3-chloroaniline (38.2 g, 0.30 mole) in n-butanol (250 ml) was refluxed overnight. After cooling in ice, the solid was collected by filtration and recrystallized from ethanol-water mixture to give 48 g (52%) of title product, m.p. 174°–175°.

Anal. Calcd. for C$_{14}$H$_{10}$Cl$_2$N$_2$S: C, 54.37; H, 3.26; N, 9.06.
Found C, 54.55; H, 3.31; N, 9.10.

What is claimed is:
1. A compound of the formula:

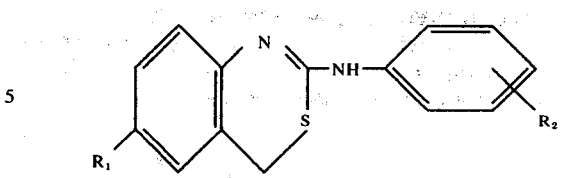

wherein R$_1$ is hydrogen and R$_2$ represents 4-dimethylamino, 5-chloro-2,4-dimethoxy or 3,4-dichloro; and R$_1$ is chloro and R$_2$ represents 4-acetyl or 3-chloro.

2. The compound 2-(4-dimethylaminoanilino)-4H-3,1-benzothiazine dihydrochloride.
3. The compound 2-(5-chloro-2,4-dimethoxyanilino)-4H-3,1-benzothiazine.
4. The compound 2-(3,4-dichloroanilino)-4H-3,1-benzothiazine.
5. The compound 2-(4-acetylanilino)-6-chloro-4H-3,1-benzothiazine.
6. The compound 6-chloro-2-(3-chloroanilino)-4H-3,1-benzothiazine.
7. The method of producing a compound of the formula:

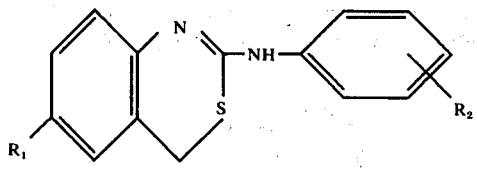

wherein R$_1$ is hydrogen and R$_2$ represents 4-dimethylamino, 5-chloro-2,4-dimethoxy or 3,4-dichloro; and R$_1$ is chloro and R$_2$ represents 4-acetyl or 3-chloro which comprises reacting a compound of the formula:

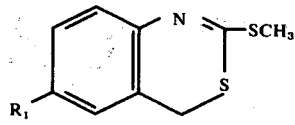

wherein R$_1$ ish hydrogen or chloro with a compound of the formula:

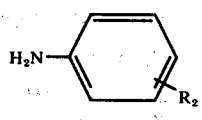

wherein R$_2$ represents 4-dimethylamino, 5-chloro-2,4-dimethoxy, 3,4-dichloro, 4-acetyl or 3-chloro.

* * * * *